United States Patent
Quinones-Garcia et al.

(10) Patent No.: US 10,669,327 B2
(45) Date of Patent: Jun. 2, 2020

(54) METHODS OF PURIFYING COLLAGEN 7

(71) Applicant: PHOENIX TISSUE REPAIR, INC., Andover, MA (US)

(72) Inventors: Igor Quinones-Garcia, Lexington, MA (US); Benjamin Simeone, Lexington, MA (US); Raymond Lillie, Lexington, MA (US); Ting Yang, Lexington, MA (US); David Nichols, Lexington, MA (US)

(73) Assignee: PHOENIX TISSUE REPAIR, INC., Boston, MA (US)

( * ) Notice: Subject to any disclaimer, the term of this patent is extended or adjusted under 35 U.S.C. 154(b) by 0 days.

(21) Appl. No.: 16/084,998

(22) PCT Filed: Mar. 10, 2017

(86) PCT No.: PCT/US2017/021815
§ 371 (c)(1),
(2) Date: Sep. 14, 2018

(87) PCT Pub. No.: WO2017/160636
PCT Pub. Date: Sep. 21, 2017

(65) Prior Publication Data
US 2019/0077845 A1 Mar. 14, 2019

Related U.S. Application Data

(60) Provisional application No. 62/309,030, filed on Mar. 16, 2016.

(51) Int. Cl.
C07K 14/78 (2006.01)
A61K 38/39 (2006.01)
C07K 1/16 (2006.01)
C07K 1/34 (2006.01)

(52) U.S. Cl.
CPC ............. *C07K 14/78* (2013.01); *A61K 38/39* (2013.01); *C07K 1/16* (2013.01); *C07K 1/34* (2013.01)

(58) Field of Classification Search
CPC .......... A61K 38/39; C07K 14/78; C07K 1/16; C07K 1/34
See application file for complete search history.

(56) References Cited

U.S. PATENT DOCUMENTS

| | | |
|---|---|---|
| 2007/0066806 A1 | 3/2007 | Coffman et al. |
| 2013/0338344 A1 | 12/2013 | Ramasubramanyan et al. |
| 2014/0275494 A1 | 9/2014 | Wang et al. |
| 2015/0353904 A1 | 12/2015 | Nichols et al. |

FOREIGN PATENT DOCUMENTS

| | | |
|---|---|---|
| WO | 2012149136 A1 | 11/2012 |
| WO | 2013020064 A1 | 2/2013 |
| WO | 2015042639 A1 | 4/2015 |

OTHER PUBLICATIONS

Huang et al. Bioreactor systems for in vitro production of foreign proteins using plant cell cultures. Biotechnology Advances, 2012. vol. 30, pp. 398-409. (Year: 2012).*
Xiong et al. Preparation and Characterization Urea-Solubilized Sol-Gel Type I Collagen and Its Possible Use in Applications. Regenerative Medicine and Tissue Engineering-Cells and Biomaterials, 2011. (Year: 2011).*
Ritala et al. Production of a recombinant industrial protein using barley cell cultures. Protein Expression and Purification, 2008, Vo. 59, pp. 274-281. (Year: 2008).*
Xiong et al. Chapter 11: Preparation and Characterization Urea-Solubilized Sol-Gel Type I Collagen and Its Possible Use . Regenerative Medicine and Tissue Engineering-Cells and Biomaterials. Edited by Prof. Daniel Eberli. pp. 245-260. (Year: 2011).*
Chen, Mei et al. "The Recombinant Expression of Full-length Type VII Collagan and Characterization of Molecular Mechanisms Underlying Dystrophic Epidermolysis Bullosa", The Journal of Biological Chemistry, vol. 277, No. 3, Jan. 18, 2002, pp. 2118-2124.
International Search Report & Written Opinion dated May 23, 2017 in co-pending application No. PCT/US2017/021815, entitled Methods of Purifying Collagen 7.
Extended EP Search Report received in corresponding EP Application No. 17767212.8 dated Oct. 9, 2019.

* cited by examiner

*Primary Examiner* — Marcela M Cordero Garcia (74) *Attorney, Agent, or Firm* — Donna T. Ward; Lingyun Jia; DT Ward, PC (57) ABSTRACT

The present disclosure provides methods for capturing recombinant collagen 7 from cell culture and methods of purifying recombinant collagen 7. Also provided are compositions comprising purified recombinant collagen 7 that may be used for administration to humans.

21 Claims, 5 Drawing Sheets

METHODS OF PURIFYING COLLAGEN 7

CROSS REFERENCE TO RELATED APPLICATIONS

This application is a 35 U.S.C. § 371 U.S. National Stage Entry of International Application No. PCT/US2017/021815, filed Mar. 10, 2017, which claims priority to U.S. Provisional Application No. 62/309,030, entitled Methods of Purifying Collagen 7, filed Mar. 16, 2016; the contents of each of which are incorporated herein by reference in their entirety.

FIELD

This disclosure relates to methods for capturing and purifying collagen 7 and compositions comprising purified collagen 7, including purified collagen 7 that may be used for administration to humans.

BACKGROUND

Collagen 7 ("C7") is a structural protein that functions to strengthen and stabilize the skin, and is a major component of anchoring fibrils, which help anchor the top layer of the skin, the epidermis, to the underlying dermis. The C7 monomer assembles as a homotrimer of approximately 900 kDa, containing one NC-1 and one NC-2 binding domains. The homotrimer is held together via an alpha helical coil. From a homotrimer, these C7 protein precursors align into an anti-parallel dimer with an increase in molecular weight to 1.8 mDa. Lateral assembly of anti-parallel dimers leads to the formation of the anchoring fibrils (about 800 nm long).

Epidermolysis bullosa (EB) is a group of genetic conditions that cause the skin to be very fragile and to blister easily. Blisters and skin erosions form in response to minor injury or friction, such as rubbing or scratching. Dystrophic epidermolysis bullosa (DEB) is one of the major forms of epidermolysis bullosa. The signs and symptoms of this condition vary widely among affected individuals. In mild cases, blistering may primarily affect the hands, feet, knees, and elbows. Severe cases of this condition involve widespread blistering that can lead to vision loss, disfigurement, and other serious medical problems. Dystrophic epidermolysis bullosa can be classified into three major types: Recessive dystrophic epidermolysis bullosa (RDEB), non-Hallopeau-Siemens type (non-HS RDEB), and autosomal dominant type (DDEB). Although the types differ in severity, their features overlap significantly and they are all caused by mutations in the COL7A1 gene, which encodes for the protein collagen 7.

The C7 homotrimer can also be purified by the solubilization of amnion using pepsin [2]. The solubilized collagens are partially fractionated by differential salt precipitation, where C7 co-precipitates with collagen 5 ("C5"). Separation of C7 from C5 can be accomplished by CM-cellulose chromatography, following removal of contaminating proteoglycans by DEA-cellulose chromatography. This product is sufficiently pure for routine laboratory use. If further purification is necessary, the pure native structure can be obtained by preparative velocity sedimentation. Pure denatured alpha chains can be obtained following HPLC reversed-phase chromatography.

rC7 has been purified at a laboratory scale by precipitation with ammonium sulfate followed by anion exchange chromatography [2]. However, the yield and purity of this purification method are not sufficient for commercial scale purification of rC7 for therapeutic purposes. Previous attempts to develop a commercial-scale purification method for rC7 had an overall yield of only about 1%.

SUMMARY

The present disclosure provides methods to prepare purified rC7. These purification methods significantly enhance the yield of rC7 over previous methods and can be used to prepare commercial-scale rC7 compositions of high purity that may be used for administration to humans.

In one aspect, the disclosure relates to a capture process for collecting and concentrating rC7 from cell culture supernatants into an unpurified bulk liquid, which is optionally frozen ("upstream processing"). In another aspect, the disclosure relates to a process for purifying rC7 in the unpurified bulk liquid ("downstream processing"). It is also possible to combine the upstream and downstream processing steps to obtain purified collagen 7 that is suitable for administration to humans. In certain embodiments, the capture and purification methods are commercial-scale methods.

The upstream processing contains a clarification step (e.g., depth filter) and a concentrating/buffer exchange step. For the upstream processing, one embodiment is directed to a method of capturing recombinant human collagen 7 produced from a cell culture, the method comprising:

a) subjecting a supernatant harvested from the cell culture to a depth filter, wherein the supernatant contains recombinant human collagen 7;

b) collecting a solution that flows through the depth filter;

c) subjecting the solution from step b) to an ultrafiltration step, wherein the recombinant human collagen 7 concentrates in a layer adjacent to the ultrafiltration membrane;

d) discarding a first retentate, wherein the first retentate comprises impurities contained in the solution from step (b);

e) subjecting the layer adjacent to the ultrafiltration membrane to a solubilization agent and/or a surfactant to recover recombinant human collagen 7 and to obtain a second retentate comprising recombinant human collagen 7;

f) subjecting the second retentate to a diafiltration step to obtain an unpurified bulk liquid comprising recombinant human collagen 7; and g) optionally freezing the unpurified bulk liquid.

In certain embodiments, the method further comprises before step a), the steps of:

a) culturing host cells that produce recombinant human collagen 7; and b) harvesting supernatant from the cultured host cells.

In certain embodiments, the unpurified bulk liquid contains 40-80% of the recombinant collagen 7 in the clarified supernatant. In one embodiment, the unpurified bulk liquid contains on average about 60% of the recombinant collagen 7 in the clarified supernatant.

In certain embodiments, the cell culture comprises culturing host cells in a bioreactor with a volume of at least 200 liters, preferably at least 1500 liters. In certain embodiments, the bioreactor is a perfusion bioreactor or a fed-batch bioreactor.

In certain embodiments, the unpurified bulk liquid contains over 50 grams of recombinant human collagen 7.

In certain embodiments, the solubilization agent comprises at least one of urea, thiourea, arginine, butanol, ethanol, lithium perchlorate, lithium acetate, magnesium acetate, phenol, propanol, sodium dodecyl sulfate, aspartic acid, glutamic, ascorbic acid, glutamine, asparagine, and guanidine. In one embodiment, the solubilization agent comprises arginine.

For the downstream processing, one embodiment is directed to a method of purifying recombinant human collagen 7, the method comprising:

a) subjecting a sample containing recombinant human collagen 7 to a mixed mode, flow through resin, wherein the mixed mode flow through resin comprises a ligand activated core and an inactive shell, wherein the inactive shell prevents recombinant human collagen 7 from entering the ligand activated core and wherein impurities that are small enough pass through the inactive shell and bind to the ligand activated core;

b) collecting a first effluent that flows through the mixed mode, flow through resin and contains recombinant human collagen 7;

c) subjecting the first effluent from step b) to a cation exchange chromatography resin under conditions permitting the recombinant human collagen 7 to bind to the cation exchange chromatography resin;

d) eluting recombinant human collagen 7 from the cation exchange chromatography resin;

e) subjecting the eluted recombinant human collagen 7 from step d) to a hydrophobic interaction chromatography resin in flow through mode and collecting a second effluent that flows through the hydrophobic interaction chromatography resin;

f) subjecting the second effluent of step e) to an ultrafiltration step to concentrate the recombinant human collagen 7;

g) dialfiltering the concentrated recombinant human collagen 7 from step f) with a buffer; and h) recovering purified recombinant human collagen 7, wherein the method comprises one or more viral reduction steps and an endonuclease treatment step.

In certain embodiments, the ultrafiltration step comprises a tangential flow filter and wherein the tangential flow filter comprises a hydrophilic membrane.

In certain embodiments, the method further comprises a step of adding a solubilization agent and/or surfactant to the second effluent from step e) prior to step f).

In certain embodiments, the one or more viral reduction steps comprise a step of irradiating (e.g., UV radiation) the sample containing recombinant human collagen 7 prior to step a), a step of adding a surfactant to the first effluent from step b), and a step of subjecting the second effluent from step e) to a porous filter. In one embodiment, the porous filter comprises a plurality of pores having a mean diameter of 35 nm.

In certain embodiments, the endonuclease treatment step comprises treating the eluted recombinant human collagen 7 from step d) with an endonuclease.

In certain embodiments, the buffer comprises at least one salt, a solubilization agent, and a sugar.

In certain embodiments, the at least one salt is one or more of sodium chloride, citrate, and sodium phosphate, the solubilization agent is arginine, and the sugar is sucrose.

In certain embodiments, the purified, recombinant human collagen 7 of step h) contains on average between 15-30% of the amount of the recombinant human collagen 7 in the sample from step a).

In certain embodiments, the sample in step a) contains at least 25 grams of recombinant human collagen 7.

In certain embodiments, at least 4.0 grams of purified, recombinant human collagen 7 is recovered in step h).

In certain embodiments, the purified recombinant human collagen 7 of step h) contains no more than 2000 ng of host cell protein per mg recombinant human collagen 7, preferably no more than 1000 ng/mg, and more preferably no more than 600 ng/mg.

In certain embodiments, the purified recombinant human collagen 7 of step h) contains no more than 42 pg host cell DNA per mg recombinant human collagen 7, preferably no more than 25 pg/mg, and more preferably no more than 15 pg/mg.

In certain embodiments, the purified recombinant human collagen 7 of step h) contains no more than 1.0 EU/mg endotoxin per mg recombinant human collagen 7, preferably no more than 0.70 EU/mg, and more preferably no more than 0.50 EU/mg.

In certain embodiments, the method further comprises before step a), the steps of:

a) subjecting a supernatant harvested from a cell culture to a depth filter, wherein the supernatant contains recombinant human collagen 7;

b) collecting a solution that flows through the depth filter;

c) subjecting the solution from step b) to an ultrafiltration step, wherein the recombinant human collagen 7 concentrates in a layer adjacent to an ultrafiltration membrane;

d) discarding a first retentate, wherein the first retentate comprises impurities contained in the solution from step (b);

e) subjecting the layer adjacent to the ultrafiltration membrane to a solubilization agent and/or a surfactant to recover recombinant human collagen 7 and to obtain a second retentate comprising recombinant human collagen 7;

f) subjecting the second retentate to a diafiltration step to obtain an unpurified bulk liquid comprising recombinant human collagen 7; and g) optionally freezing the unpurified bulk liquid.

In certain embodiments, the solubilization agent comprises at least one of urea, thiourea, arginine, butanol, ethanol, lithium perchlorate, lithium acetate, magnesium acetate, phenol, propanol, sodium dodecyl sulfate, aspartic acid, glutamic, ascorbic acid, glutamine, asparagine, and guanidine. In one embodiment, the solubilization agent comprises arginine.

Another aspect is directed to purified rC7 compositions obtained by the methods described herein. The purified rC7 compositions are preferably suitable for human use. In certain embodiments, the rC7 composition contains:

no more than 2000 ng of host cell protein per mg rC7, preferably no more than 1000 ng/mg, and more preferably no more than 600 ng/mg;

no more than 42 pg host cell DNA per mg rC7, preferably no more than 25 pg/mg, and more preferably no more than 15 pg/mg.; and/or no more than 1.0 EU/mg endotoxin per mg rC7, preferably no more than 0.70 EU/mg, and more preferably no more than 0.50 EU/mg.

Both the foregoing general summary and the following detailed description are exemplary only and are not restrictive of the disclosure.

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

DETAILED DESCRIPTION

1. Definitions

In order for the present invention to be more readily understood, certain terms are first defined below. Additional definitions for the following terms and other terms are set forth through the specification.

As used in this specification and the appended claims, the singular forms "a," "an," and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Commercial Scale: As used herein, the term "commercial scale" is used to distinguish large-scale production methods from bench scale methods, which are often difficult to scale to obtain levels of rC7 production sufficient for commercial purposes. Commercial scale capture and purification methods result in gram quantities of rC7.

Excipient: As used herein, the term "excipient" refers to a non-therapeutic agent that may be included in a pharmaceutical composition, for example to provide or contribute to a desired consistency or stabilizing effect. Suitable pharmaceutical excipients include, for example, a buffer (e.g., phosphate buffer, such as sodium phosphate, Tris buffer), saline, a salt (e.g., sodium chloride), lactated Ringer's, electrolytes, surfactants (e.g., a surfactant, such as polysorbate, triton X-100), stabilizers, preservatives, such as anti-microbials or antioxidants, starch, a sugar (e.g., glucose, lactose, sucrose, Ringer's dextrose, and dextrose) gelatin, malt, rice, flour, chalk, silica gel, sodium stearate, glycerol monostearate, talc, dried skim milk, glycerol, propylene, glycol, water, ethanol and the like.

Host cell: As used herein, the phrase "host cell" refers to a cell into which exogenous DNA (recombinant or otherwise) has been introduced, such as DNA encoding human collagen 7. Host cells may be used to produce a polypeptide of interest, such as human collagen 7, by standard recombinant techniques. Persons of skill upon reading this disclosure will understand that such terms refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include any prokaryotic and eukaryotic cells suitable for expressing an exogenous DNA (e.g., a recombinant nucleic acid sequence). Exemplary cells include non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15$^{th}$ Edition (1975), describes compositions and formulations suitable for pharmaceutical delivery of one or more therapeutic compositions, such as one or more influenza vaccines, and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Recombinant: As used herein, the term "recombinant" is intended to refer to polypeptides (e.g., collagen 7 polypeptides as described herein) or nucleic acids encoding the same that are designed, engineered, prepared, expressed, created or isolated by recombinant means, such as polypeptides expressed using a recombinant expression vector transfected into a host cell, polypeptides isolated from a recombinant, combinatorial polypeptide library or polypeptides prepared, expressed, created or isolated by any other means that involves splicing selected sequence elements to one another. Standard techniques may be used for recombinant nucleic acids, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art. See e.g., Sambrook et al. Molecular Cloning: A Laboratory Manual (4th ed., Cold Spring Harbor Laboratory Press, Cold Spring Harbor, N.Y. (2012)), which is incorporated herein by reference.

Surfactant: As used herein, the term "surfactant" refers to a compound that lowers the surface tension between two liquids or between a liquid and a solid. Examples of a surfactant include, but are not limited to, polyoxyethylene sorbitan ester (generally referred to as Tweens), in particular, polysorbate 20 and polysorbate 80; copolymers (such as DOWFAX) of ethylene oxide (EO), propylene oxide (PO), butylenes oxide (BO); octoxynols with different repeats of ethoxy(oxy-1,2-ethanediyl) group, in particular, octoxynol-9 (Triton X-100); ethylphenoxypolyethoxyethanol (IGEPAL CA-630/NP-40); phospholipid such as lecithin; nonylphenol ethoxylate such as TERGITOL NP series; lauryl, cetyl, stearyl, oleyl alcohol-derived polyoxyethylene fatty ether (Brij surfactant), in particular, triethyleneglycol monolauryl ether (Brij 30); sorbitan ether known as SPAN, in particular, sorbitan trioleate (Span 85) and sorbitan monolaurate.

2. Overview

In order to advance development of rC7 beyond animal models and into clinical studies, a scalable process capable of producing rC7 for human use was developed. When trying to develop a process for purifying rC7 from large-scale cell culture, the current inventors discovered that the rC7 demonstrated "stickiness," and the propensity to precipitate at higher protein concentrations, particularly when formulated in PBS buffer, limiting the solubility of rC7 and resulting in the loss of a significant amount of protein during commercial-scale purification methods. The solubility of the rC7 in PBS buffer was limited to about 0.4 mg/mL, with significant precipitation and viscosity issues above 0.4 mg/mL. It was possible to increase the solubility rC7 in PBS buffer to about 0.8 mg/mL, but only under very specific lab conditions that were not scalable or compatible with conventional purification processes, such as ultrafiltration/diafiltration (UF/DF).

Figure 4:
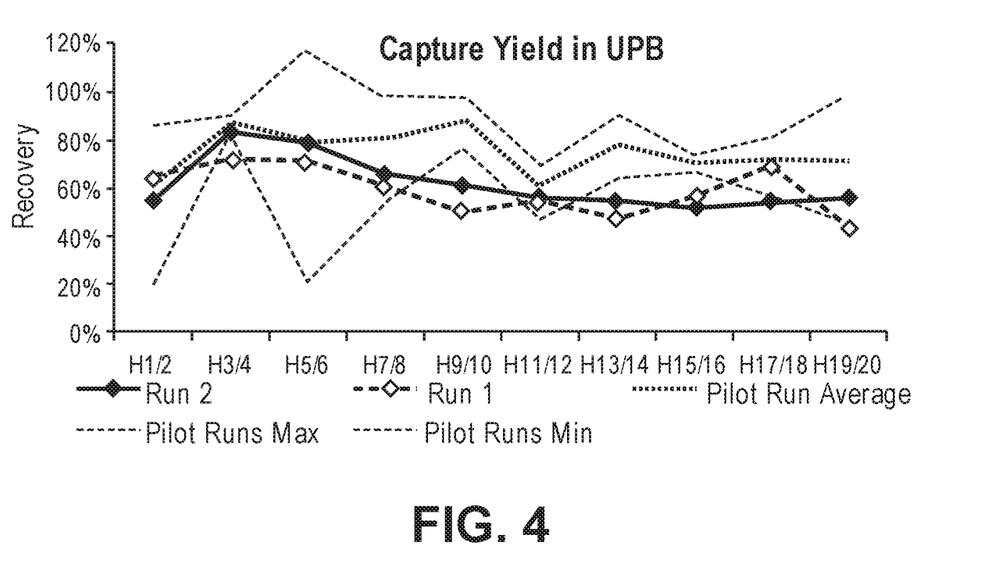
FIG. 4 shows the percentage rC7 recovery in the unpurified bulk (UPB) obtained from the harvests of a first and second production run (20 daily harvests total for each run), following the clarification and UF/DF steps (upstream process). Average rC7 yield ratios (and maximum and minimum values) from pilot runs are also provided.

The current inventors developed a rC7 purification process, achieving significantly higher yields than capable with previous methods. The purified rC7 was highly purified and retained potency. The purification process is separated into two parts: an upstream process to capture rC7 harvested from large scale cell culture followed by a downstream process to purify the captured rC7. The capture process includes a clarification step and a concentration step (typically an ultrafiltration/diafiltration or "UF/DF" step), where harvested cell culture supernatant containing rC7 is passed through an ultrafiltration membrane. Rather than collecting the rC7 in the retentate as carried out in our prior attempts to develop a commercial-scale purification method for rC7, the initial retentate was discarded to remove impurities. Without intending to be bound by any theory, it appears that under these conditions rC7 concentrates in a layer adjacent to the ultrafiltration membrane and not in the retentate. After discarding the initial retentate, the layer is subjected to a solubilization agent and/or surfactant to recover the rC7. Without intending to be bound by any theory, it appears that the solubilization agent and/or surfactant helps to solubilize the rC7 in the layer. In this way, the rC7 is released from the layer and collected in a second retentate, which is subjected to a diafiltration step to obtain an unpurified bulk liquid comprising recombinant human collagen 7. The yield of this initial UF/DF step averaged about 60% (see e.g., FIG. 4), as compared to about 24% when using an earlier, internal capture method where the rC7 was collected in the initial retentate of an ultrafiltration membrane, leading to significantly lower yields.

The rC7 can be further purified by subjecting the unpurified bulk liquid from the upstream processing to a mixed mode, flow through resin, followed by a cation exchange chromatography resin in bind and elute mode, followed by a hydrophobic interaction chromatography resin in flow through mode, and a final UF/DF step. In certain embodiments, the purification method also contains one or more viral reduction steps and an endonuclease treatment step. The rC7 recovered from this purification process is highly purified and retains fibronectin binding activity. The overall yield of the downstream process averaged 20%, a significant improvement as compared to about 2% obtained by an earlier, internal downstream process for commercial-scale purification of rC7. In addition, this purification scheme yields rC7 that is sufficiently pure with respect to residual host cell DNA and protein for testing or use in humans (i.e., less than 100 pg host cell DNA per therapeutic dose and more preferably less than 10 pg per dose). The methods disclosed herein are designed primarily for capturing and purifying rC7 at a commercial scale.

In one aspect, the present disclosure provides a method for capturing rC7, the method comprising:
 a) clarifying harvested cell culture supernatant containing rC7 (e.g., using a depth filter);
 b) concentrating the clarified rC7 composition (e.g., using an ultrafiltration membrane)
 c) diafiltering the concentrated rC7 composition; and
 g) optionally freezing the unpurified bulk liquid.

In certain embodiments, the method further comprises before step a), the steps of:
 a) culturing host cells that produce rC7; and
 b) harvesting supernatant from the cultured host cells.

In another aspect, the present disclosure provides a method of purifying rC7, the method comprising:
 a) subjecting a sample containing rC7 to:
  a mixed mode chromatography, flow through resin;
  a cation exchange chromatography resin;
  a hydrophobic interaction chromatography (HIC) resin in flow through mode;
 b) concentrating the rC7 in the effluent from the HIC resin (e.g., using an ultrafiltration membrane);
 c) dialfiltering the concentrated rC7 composition; and
 d) recovering purified rC7.

The purification method optionally includes one or more viral reduction steps and an endonuclease treatment step.

Various features and embodiments of these capture and purification methods are described in further detail below.

3. Cell Culture rC7 can be produced at a commercial scale using standard cell culture procedures known to those skilled in the art. Typically, a nucleic acid encoding rC7 is introduced into a host cell and the host cell is propagated under appropriate cell culture conditions. The collagen 7 is preferably human collagen 7. Nucleic acid sequences encoding human collagen 7 are known in the art. rC7 is secreted into the cell culture supernatant. For commercial scale production of rC7, culture cells are typically grown in large bioreactors. In certain embodiments, the bioreactor is a perfusion bioreactor. In other embodiments, the bioreactor is a fed-batch bioreactor. In certain embodiments, the cell culture comprises culturing host cells in a bioreactor with a cell culture volume of at least 200, at least 500, at least 1000, at least 1500, at least 2000, at least 2500, at least 5000, at least 10,000, at least 15,000, or at least 20,000 liters. In certain embodiments, the bioreactor is a perfusion bioreactor and the volume of the cell culture in the perfusion bioreactor is at least 200 liters, and more preferably at least 1500 liters.

Typically, rC7 is expressed in a continuous cell line. More typically, the continuous cell line is a mammalian cell line. Suitable continuous cell lines include, for example, Chinese Hamster Ovary (CHO), mouse myeloma (e.g., NS0), baby hamster kidney (BHK), human embryo kidney (e.g., HEK-293), C127, VERO, HeLa, COS, and Madin-Darby Canine Kidney Epithelial cells (MDCK). See e.g., U.S. Pat. No. 6,632,637, which is hereby incorporated by reference in its entirety. Other suitable host cells are known to those skilled in the art. In one embodiment, rC7 is expressed in CHO cells. In another embodiment, rC7 is expressed in HEK-293 cells.

4. Upstream Process

Figure 1:
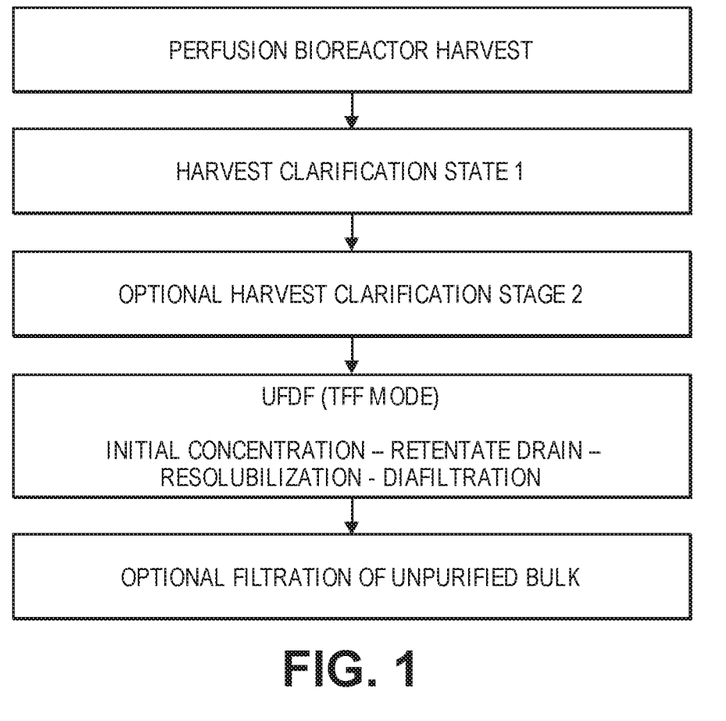
FIG. 1 is a flow chart showing one embodiment of the general upstream process for harvesting, clarifying, and concentrating (UF/DF) rC7 into an unpurified bulk liquid.
Figure 2:
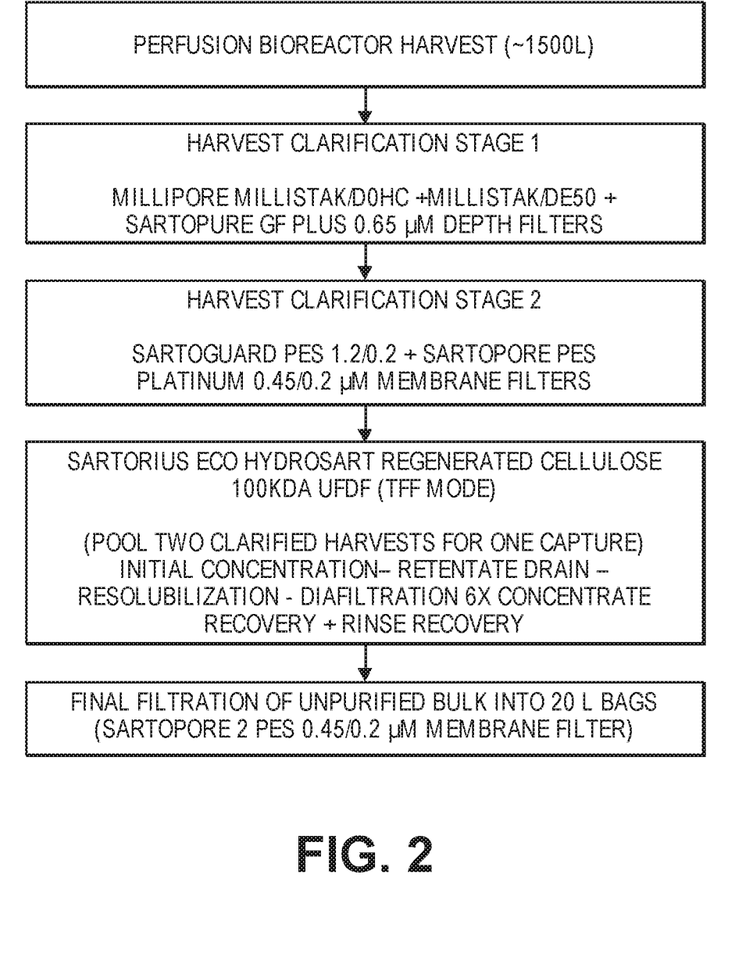
FIG. 2 is a flow chart showing one embodiment of a specific upstream process for harvesting, clarifying, and concentrating (UF/DF) rC7 into an unpurified bulk liquid.

In one aspect, the disclose relates to a capture process for collecting and concentrating rC7 from cell culture supernatants into an unpurified bulk liquid, which is optionally frozen. This aspect is also referred to as upstream processing, in which rC7 is harvested, clarified, and concentrated. A flow chart showing one embodiment of the general upstream process is shown in FIG. 1. FIG. 2 shows one embodiment of a specific upstream process used to capture rC7.

a. Harvest

Supernatant from the bioreactor is collected and maintained at an appropriate storage temperature, typically, 2-8° C. Typically, the unprocessed supernatant is held less than 1 day before starting the clarification process. If cells are grown in a perfusion bioreactor, supernatant is harvested as a batch on a daily basis for 5-30, 10-25, or 15-20 days, preferably 20 days.

b. Clarification

The harvested supernatants may be clarified to remove, for example, intact cells and cellular debris and to reduce bioburden and other particulates prior to the UF/DF step. Any clarification process known to an ordinary artisan may be used including filtration, microfiltration, centrifugation, chromatography and the like.

Typically, filtration is used to remove cell debris and intact cells from the harvested supernatant. As is known in the art, the choice of filtration process will be a function, in part, of the contaminant size distribution relative to the size of the protein to be retained. The desired filtration option will optimize the balance between removing the unwanted residual particles while maintaining a high rC7 yield. Suitable filters include cellulose filters, regenerated cellulose fibers, cellulose fibers combined with inorganic filter aids, cellulose fibers combined with inorganic filter aids and organic resins, or any combination thereof.

In some embodiments, clarification of the harvested supernatant is performed using a depth filtration procedure. As understood in the art, depth filtration refers to the use of a porous filter medium to clarify solutions containing significant quantities of large particles (e.g., intact cells or cellular debris) in comparison to membrane filtration which may rapidly become clogged under such conditions. A depth filtration step may involve passing a fluid through one or more, two or more or three or more depth filters. In certain embodiments, the upstream processing includes two clarification steps, where the first clarification step generally uses a depth filter with a larger pore size (e.g., 65 µm) and the second clarification step generally uses a sterilizing grade membrane filter with a smaller pore size (e.g., 0.45 and/or 0.2 µm).

A variety of depth filtration media of varying pore sizes are commercially available from a variety of manufacturers such as Millipore, Pall, General Electric, and Sartorious. For example, Millistak/DOHC and Millistak/DE50 (EMD Millipore, Darmstadt, Germany) and Sartopure GF Plus (0.65 µm depth filter) may be used. A variety of membrane filters of varying pore sizes are commercially available from a variety of manufacturers such as Millipore, Pall, General Electric, and Sartorious. For example, Sartoguard PES 1.2/ 0.2 µm, Sartopore PES Platinum 0.45/0.2 µm filters (Sartorious Stedim, Goettingen, Germany) may be used.

c. Concentration and Buffer Exchange

In certain embodiments of the upstream process, a rC7 composition is concentrated by any one of a number of processes known to those of ordinary skill in the art, e.g., dialysis, chromatography, ultrafiltration and the like.

In one embodiment, a rC7 composition is concentrated by ultrafiltration before being subjected to a diafiltration step ("UF/DF"). UF/DF is a combined operation of ultrafiltration and diafiltration. The step removes impurities and/or components that are smaller in molecular size than the porosity or molecular weight cut off (MWCO) of the membrane, concentrates the rC7, and exchanges/modifies the aqueous or buffer composition of the rC7 composition. Though well known in the art, for clarity the term "ultrafiltration" refers to the process of separating impurities from the rC7 by passing the composition through one or more semi-permeable filter(s) (or membrane or medium) of a specified pore size diameter, where larger molecules are retained on the filter, while water and lower molecular weight molecules pass through the filter. These lower molecular weight molecules could be media components, peptide fragments, and/or other contaminants (impurities) such as, e.g., lipopolysaccharides, smaller molecular weight host cell proteins. Membrane pore size is selected based on the size of the target molecule. In general, particles larger than the MWCO will be retained by the membrane, while particles smaller than the MWCO will pass through. This process also concentrates the rC7 composition.

The term "permeate stream" when referring to filtration refers to the fraction of the composition that passes through the filter pores during filtration. The term "retentate stream" when referring to filtration refers to the fraction of the composition that remains on the filter or that does not pass through the filter pores during filtration.

In our previous, internal, large-scale capture processes, rC7 was collected in the retentate stream, while impurities are in the permeate stream that is discarded. By contrast, in the current methods, in the ultrafiltration step of the upstream process, the initial retentate stream is discarded, along with the permeate stream. Without intending to be bound by any theory, it appears that under these conditions rC7 concentrates in a layer adjacent to the ultrafiltration membrane and is collected in neither the initial retentate stream nor the permeate stream. After discarding the initial retentate, the layer was subjected to a solubilization agent and/or surfactant to recover the rC7. Without intending to be bound by any theory, it appears that the solubilization agent and/or surfactant helps to solubilize the rC7 in the layer. In this way, the rC7 is released from the layer and collected in a second retentate, which is subjected to a diafiltration step to obtain an unpurified bulk liquid comprising rC7.

Suitable types of UF/DF membranes and apparatuses are known to those in the art and can be selected based on various factors, e.g., the molecular weight of the protein to be filtered, the amount and size of the components of the composition to be filtered, the volume of the composition to be filtered, and the cell density and viability of the composition to be filtered. In some embodiments, filters, such as membrane ultrafilters, plate ultrafilters, cartridge ultrafilters, bag ultrafilters, or vacuum ultrafilters can be used. In certain embodiments, the MWCO of the ultrafiltration membrane or filter is between 250-50 kDa, preferably about 200 kDa or 100 kDa. In certain embodiments, the ultrafiltration membrane or filter comprises cellulose acetate, regenerated cellulose, polyvinylidene fluoride (PVDF), or polyethersulfone (PES). In one embodiment of the UF/DF step in the upstream process, the ultrafiltration membrane comprises cellulose or regenerated cellulose.

In certain embodiments, the ultrafiltration step produces a rC7 composition with a concentration of rC7 greater than 10 times, 20 times, 30 times, 40 times, 50 times, 60 times, 70 times, 80 times, 90 times, or 100 times, 120 time, 150 times, or 200 times the concentration of rC7 present in the harvested supernatant.

Commercially available ultrafiltration membranes or filters that can be used are manufactured by various vendors such as Millipore Corporation (Billerica, Mass.), Pall Corporation (East Hills, N.Y.), GE Healthcare Sciences (Piscataway, N.J.), and Sartorius Corporation (Goettingen, Germany). For example, Satorius ECO regenerated cellulose (100 kDa) may be used.

Typically, ultrafiltration/diafiltration is conducted via Tangential Flow Filtration (TFF) mode. TFF (also referred to as Cross Flow Filtration (CFF)) is well known to those of ordinary skill in the art and equipment and protocols for its implementation in a wide range of situations are commercially available from a variety of manufacturers including but not limited to the Pall Corporation (Port Washington, N.Y.) and Spectrum Labs (Rancho Dominguez, Calif.). Generally, TFF involves the recirculation of the retentate across the surface of the membrane. This gentle cross flow feed minimizes membrane fouling, maintains a high filtration rate and provides high product recovery. In one embodiment, TFF may be implemented with a flat sheet system. In another embodiment, TFF may be implemented with a hollow fiber system, as exemplified herein.

The diafiltration serves to prepare the rC7 composition for its end use, such as storage, lyophilization, parenteral formulation, etc. The buffer system is typically exchanged and/or modified by adding/removing/replacing buffering agents and/or their concentration to produce an unpurified bulk liquid comprising rC7. Additional additives can be introduced, for example to adjust pH, tonicity, solubility, and/or stability. Stability can refer to stabilizing the rC7 composition in the liquid state or to protecting the rC7 during lyophilization or reconstitution. In certain embodiments, the unpurified bulk liquid comprises recombinant collagen 7, a Tris buffer, a solubilization agent (e.g., arginine), sodium chloride and a surfactant (e.g., triton X-100). The unpurified bulk (UPB) liquid can be stored or frozen for subsequent use.

In certain embodiments, the UPB liquid contains 40-80% of the rC7 in the supernatant harvested from the cell culture. In certain embodiments, the average rC7 recovery for the clarification and capture step is about 40-45%, i.e., pooled UPB contains about 40-45% of the rC7 in the supernatant harvested from the cell culture. In certain embodiments, the UPB liquid contains over 5, 10, 15, 20, 25, 30, 35, 40, 45, 50, 60, 70, 80, 90, or 100 grams of rC7.

d. Sterile Filtration

A sterile filtration step may also be included in the present method, which is helpful in eliminating bioburden. For example, following the UF/DF step, the UPB can be sterile filtered using, for example, a 0.22 micron filter, such as a modified polyvinylidene fluoride (PVDF) membrane (EMD Millipore). In addition to modified PVDF, the sterile filter may be constructed of a variety of other materials that are well known in the art and available to the ordinary artisan. These may include but are not limited to polypropylene, cellulose, cellulose esters, nylon, polyethersulfone, or any other material, which is consistent with low product binding. The sterile filtered rC7 composition can be frozen and stored or held at 2-8° C. until ready for subsequent use.

5. Downstream Process

Figure 3:
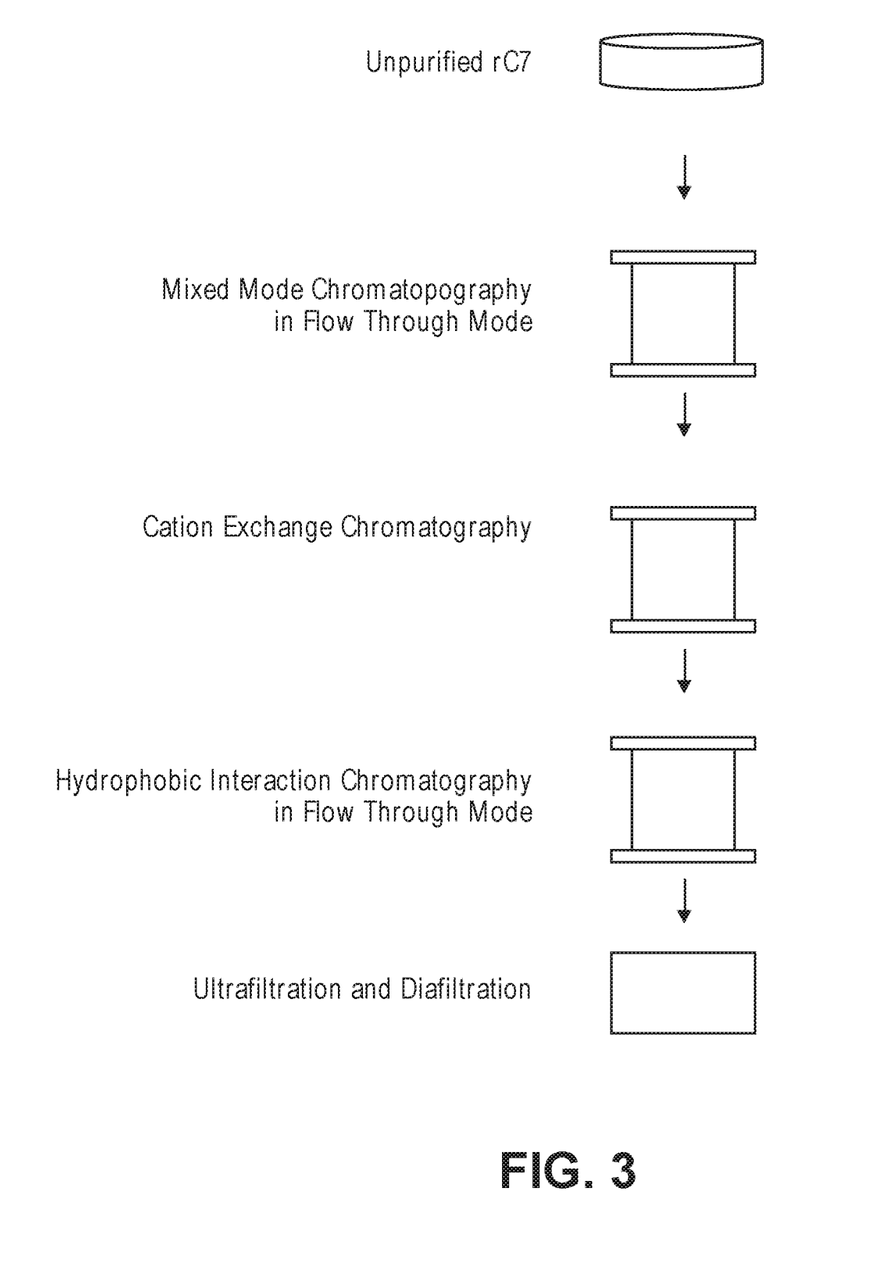
FIG. 3 is a flow chart showing an embodiment of the general downstream process for purifying rC7 by subjecting the rC7 to a mixed mode, flow through resin, followed by cation exchange chromatography, a hydrophobic interaction chromatography resin in flow through mode, and a final UF/DF step.

Any rC7 sample, including rC7 collected by any capture process, can be further purified by subjecting the rC7 sample to a mixed mode, flow through resin, followed by cation exchange chromatography, a hydrophobic interaction chromatography resin in flow through mode, and a final concentration and optional buffer exchange (e.g., UF/DF) step. FIG. 3. The purification method also preferably contains one or more viral reduction steps and an endonuclease treatment step. The rC7 recovered from this purification process is highly purified and retains fibronectin binding activity. The purified rC7 is preferably suitable for human use.

a. Mixed Mode Chromatography

The mixed mode flow through resin combines two general purification techniques: size exclusion and binding separation. The mixed mode flow through resin comprises a ligand activated core and an inactive shell. The inactive shell functions as the size exclusion component and prevents larger molecules, such as rC7, from entering the ligand activated core. The inactive shell has different pore sizes to set the desired molecular weight cut off. In certain embodiments, the molecular weight cut off of the inactive shell is between 200 and 1500 kDa, more preferably between 500-900 kDa, and most preferably about 700 kDa.

Larger molecules, like rC7, are collected in the column flow through while smaller impurities pass through the inactive shell, enter the ligand activated core and bind to the internalized ligands. The core is functionalized with ligands that determine the binding interaction. A "ligand" is a functional group that is attached to the chromatography matrix and that determines the binding properties of the matrix. Examples of "ligands" include, but are not limited to, ion exchange groups (anion or cation exchange groups), hydrophobic interaction groups, affinity groups, or combinations thereof (multimodal). Multimodal ligands promote strong binding with most impurities over a wide range of pH and salt concentrations. Bound impurities are removed from the core ligands by cleaning-in-place procedures using standard reagents, such as NaOH, and in most cases, a solvent.

Commercially available mixed mode flow through resins that can be used are manufactured by various vendors such as GE Healthcare Sciences (Piscataway, N.J.), Bio-Rad (Hercules, Calif.), and Thermo Fisher Scientific (Waltham, Mass.). For example, the GE Healthcare Sciences Capto™ Core 700 column may be used.

b. Cation Exchange Chromatography

The principles of cation exchange chromatography are well known in the art, but, briefly, this method relies on the electrostatic interactions between the particles to be isolated and the resin used. The cation exchange column contains immobilized negatively charged moieties. Because rC7 is positively charged at physiological pH ranges, the column is operated in the bind and elute mode with the rC7 binding to the cation exchange chromatography resin.

To optimize binding of positively charged molecules, the mobile phase is generally a low to medium ionic strength (i.e., low to medium salt concentration) solution. The adsorption of the molecules to the solid support is driven by the ionic interaction between the oppositely charged ionic groups in the sample molecule and in the functional ligand on the support. The strength of the interaction is determined by the number and location of the charges on the molecule and on the functional group. By increasing the salt concentration (generally by using a linear salt gradient or a step isocratic elution) the molecules with the weakest ionic interactions start to elute from the column first. Molecules that have a stronger ionic interaction require a higher salt concentration and elute later in the gradient.

A cation exchange matrix generally comprises covalently bound, negatively charged moieties. Weak or strong cation exchange resins may be employed. Commonly, strong cation exchange resins comprise supported organic groups comprising sulphonic acid or sulphonate groups or phosphoryl groups, depending upon the pH. Weak cation exchanger resins commonly comprise supported organic groups comprising carboxylic acid or carboxylate groups, depending upon the pH. In certain embodiments, multimodal cation exchange resins can be used, which incorporate additional binding mechanisms as well as the ionic interactions, for example one or more of hydrogen bonding interactions and hydrophobic interactions. Examples of suitable cation exchange resins include, but are not limited to Fractogel, carboxymethyl (CM), sulfoethyl (SE), sulfopropyl (SP), phosphate (P) and sulfonate(S), PROPAC WCX-10™ (Dionex), Capto S, Fractogel EMD SO3M, Toyopearl Megacap II SP 550C, Poros 50 HS, and SP-Sepharose FF matrix. In certain embodiments, the cation resin comprises sulfopropyl groups.

The cation exchange chromatography step should be used in bind and elute mode with respect to rC7. In bind and elute mode, rC7 is adsorbed to the cation exchange matrix, while one or more impurities flow through the matrix, thus separating rC7 from the impurities. In some embodiments, the cation exchange matrix is washed one or more times with a buffer to remove additional impurities before the adsorbed rC7 is removed from the anion exchange matrix. After one or more impurities have been removed from a composition using cation exchange chromatography in binding mode, the adsorbed rC7 can be removed (eluted) from the cation exchange matrix.

c. Hydrophobic Interaction Chromatography

Hydrophobic interaction chromatography (HIC) separates molecules based on their hydrophobicity. HIC separates molecules according to differences in their surface hydrophobicity by using a reversible interaction between these molecules and the hydrophobic surface of an HIC resin (e.g., polymeric matrix modified with hydrophobic ligands). Typically, the interaction between hydrophobic molecules and ligands of an HIC matrix is influenced by the presence of kosmotropic salts in the running buffer. A high salt concentration enhances the interaction, while lowering the salt concentration weakens the interaction. As the ionic strength of the buffer is reduced, the interaction between the molecule and the matrix is reversed, and the molecule with the lowest degree of hydrophobicity is eluted first. The most hydrophobic molecule elutes last, requiring a greater reduction in salt concentration to reverse the interaction.

Most proteins, and to a much lesser extent hydrophilic molecules (e.g., DNA and carbohydrates), have hydrophobic areas or patches on their surface. Solvation of these patches is energetically unfavorable and results in the formation of hydrophobic cavities in the aqueous mobile phase. The promotion of the hydrophobic effect (by addition of kosmotropic salts) drives the adsorption of hydrophobic areas on a protein to the hydrophobic areas on the stationary phase (e.g., those areas of the matrix that contain hydrophobic ligands). This is thermodynamically favorable in that it reduces the number and volume of individual hydrophobic cavities. In conventional HIC, reducing hydrophobic interactions by decreasing the concentration of kosmotropic salts results in de-sorption from the solid support. Conventional HIC differs from other chromatographic separation methods in that proteins bind to the stationary phase at high salt concentration and elute at low salt concentration.

HIC can also be used in "flow-through mode." HIC in flow through mode can be used to remove aggregates and other impurities. These impurities have chemical properties very similar to rC7, but they are generally more hydrophobic than rC7. Under appropriate conditions, impurities bind to the HIC resin allowing rC7 to flow through. In the HIC flow through mode, a hydrophobic chromatography/HIC resin is combined with an aqueous mobile phase buffer, typically having a pH of 5.0 to about 7.0, 5.5 to about 6.5, or about 6.0.

The most widely used HIC matrices are hydrophilic carbohydrates: cross-linked agarose and synthetic copolymer materials. The selectivity between different matrices will not be identical though the ligands may be the same. Examples of HIC matrices include, but are not limited to, agarose, sepharose and methacrylic polymers.

HIC matrices may be modified with (e.g., covalently bound by) hydrophobic ligand groups, to which hydrophobic areas of a molecule adsorb. A molecule's adsorption behavior is determined by the type of immobilized ligand. In general, straight chain alkyl ligands demonstrate hydrophobic character while aryl ligands show a mixed mode behavior where both aromatic and hydrophobic interactions are possible. The choice of ligand type may, in some instances, be empirically determined. Examples of hydrophobic ligands that may be used herein include, without limitation, ether groups, polypropylene glycol groups, phenyl groups, butyl groups, hexyl groups and octyl groups. Examples of HIC resins with these functional groups include, but are not limited to, Phenyl Sepharose, Butyl Sepharose, Octyl Sepharose, Capto Phenyl, Toyopearl Butyl, Toyopearl Phenyl, Toyopearl Hexyl, Toyopearl Ether, and Toyopearl PPG. In certain embodiments, the HIC resin comprises a methacrylic polymer modified with a polyether ligand, such as polypropylene glycol.

d. Concentration and Buffer Exchange

In certain embodiments of the downstream process, a rC7 composition is concentrated by any one of a number of processes known to those of ordinary skill in the art, e.g., dialysis, chromatography, ultrafiltration and the like.

In one embodiment, a rC7 composition is concentrated by ultrafiltration before being subjected to a diafiltration step ("UF/DF"). As discussed above, the UF/DF step removes impurities and/or components that are smaller in molecular size than the porosity of the membrane, concentrates the rC7, and exchanges/modifies the aqueous or buffer composition of the rC7 composition. In certain embodiments, the UF/DF step comprises a first ultrafiltration, a diafiltration and a second ultrafiltration using a membrane having a reduced surface area.

In certain embodiments, the effluent from the hydrophobic interaction chromatography step is treated with a solubilization agent and/or surfactant, such as arginine, prior to the UF/DF step. In these embodiments, the permeate stream is discarded, while the rC7 is concentrated in the initial retentate, which is subject to a subsequent diafiltration step.

In other embodiments, if the solubilization agent and/or detergent is not added to the rC7 composition before the UF/DF step, the initial retentate stream can be discarded, along with the permeate stream, as in the upstream process. After discarding the initial retentate, the layer can be subjected to a solubilization agent and/or surfactant, such as arginine, to recover the rC7 in a second retentate, which is subjected to a diafiltration step to obtain purified rC7.

Suitable types of UF/DF membranes and apparatuses are known to those in the art and can be selected based on various factors, e.g., the molecular weight of the protein to be filtered, the amount and size of the components of the composition to be filtered, the volume of the composition to be filtered, and the cell density and viability of the composition to be filtered. In some embodiments, filters, such as membrane ultrafilters, plate ultrafilters, cartridge ultrafilters, bag ultrafilters, or vacuum ultrafilters can be used. In certain embodiments, the MWCO of the ultrafiltration membrane or filter is between 250-50 kDa, preferably about 200 kDa or 100 kDa. In certain embodiments, the ultrafiltration membrane or filter comprises cellulose acetate, regenerated cellulose, polyvinylidene fluoride (PVDF), or polyethersulfone (PES). In one embodiment, the ultrafiltration membrane is hydrophilic. In one embodiment of the UF/DF step in the downstream process, the hydrophilic ultrafiltration membrane comprises PES.

In certain embodiments, the ultrafiltration step produces a rC7 composition with a concentration of rC7 greater than 10 times, 20 times, 30 times, 40 times, 50 times, 60 times, 70 times, 80 times, 90 times, or 100 times, 120 time, 150 times, or 200 times the concentration of rC7 present in the rC7 composition before the UF/DF step. In certain embodiments, the purified rC7 obtained after the UF/DF step in the downstream process contains on average 15-30%, or 17-21%, or about 20% of the amount of rC7 in the sample subjected to the mixed mode chromatography step. In certain embodiments, the sample subjected to the mixed mode chromatography step contains at least 15, 20, 25, 30 or 50 grams of rC7, more preferably at least 20-30 grams, or at least 25 grams. In certain embodiments, at least 2.5, 3.0, 3.5, 4.0, 4.5, or 5.0 grams of rC7, more preferably at least 3.0 to 5.0 grams, or at least 4.0 grams of rC7 are recovered from the UF/DF step in the downstream process. The purified rC7 retains fibronectin binding activity.

Commercially available ultrafiltration membranes or filters that can be used are manufactured by various vendors such as EMD Millipore (Darmstadt, Germany), Pall Corporation (East Hills, N.Y.), GE Healthcare Sciences (Piscataway, N.J.), and Sartorius Corporation (Goettingen, Germany). For example, a Biomax Pellicon 2 100 kDa (EMD Millipore, Darmstadt, Germany), may be used.

The diafiltration serves to prepare the rC7 composition for its end use, such as storage, lyophilization, parenteral formulation, etc. The buffer system is typically exchanged and/or modified by adding/removing/replacing buffering agents and/or their concentration to produce a purified rC7 composition, and preferably a rC7 composition that is suitable for human use.

The diafiltration need not place the composition in final pharmaceutical form nor provide every excipient. Additional excipients or complete changing of the composition can be carried out after UF/DF. Nevertheless, the UF/DF step generally places the rC7 composition in near-final form. Additional additives can be introduced, for example to adjust pH, tonicity, solubility, and/or stability. Stability can refer to stabilizing the rC7 composition in the liquid state or to protecting the rC7 during lyophilization or reconstitution. The purified rC7 can be stored or frozen for subsequent use. Alternatively, the purified rC7 can be lyophilized and stored for subsequent use.

e. Sterile Filtration

A sterile filtration step may also be included in the present method, which is helpful in eliminating bioburden. For example, following the UF/DF step, the purified rC7 composition can be sterile filtered using, for example, a 0.22 micron filter, such as a modified polyvinylidene fluoride (PVDF) membrane (e.g., EMD Millipore). In addition to modified PVDF, the sterile filter may be constructed of a variety of other materials that are well known in the art and available to the ordinary artisan. These may include but are not limited to polypropylene, cellulose, cellulose esters, nylon, polyethersulfone, or any other material, which is consistent with low product binding. In certain embodiments, a surfactant (e.g., polysorbate) is added to the rC7 composition before or after sterile filtration, preferably before. In certain embodiments, the surfactant (e.g., polysorbate) is added to a final concentration of 2 to 0.01% v/v, 1.0 to 0.05% v/v, or about 0.05% v/v. The sterile filtered rC7 composition can be frozen and stored or held at 2-8° C. for subsequent formulation, if desired.

f. Virus Reduction

In certain embodiments, the downstream process includes one or more viral reduction steps. A virus is "reduced" when it is either inactivated or physically removed from the composition (or both). In some embodiments, a viral reduction step is carried out before the mixed mode flow through step. In some embodiments, a viral reduction step is carried out after the mixed mode flow through step. In some embodiments, a viral reduction step is carried out both before and after the mixed mode flow through step. In some embodiments, a viral reduction step is carried out after the hydrophobic interaction chromatography step and before the UF/DF step. In some embodiments, a first viral reduction step is carried out before the mixed mode flow through step, a second viral reduction step is carried out after the mixed mode flow through step and before the hydrophobic interaction chromatography step, and a third viral reduction step is carried out after the hydrophobic interaction chromatography step and before the UF/DF step.

When referring to the inactivation of viruses, the viruses may remain in the final product, but in a non-infective form. The virus inactivation step may comprise a pH inactivation step and/or a chemical inactivation step. The chemical inactivation step can include treatment with surfactants (e.g., detergents), irradiation, and/or brief exposures to high temperatures sufficient to inactivate a virus. These methods of viral inactivation are known to those of skill in the art, and one of skill in the art can select an appropriate treatment condition. In certain embodiments, the downstream processing includes an irradiation step, preferably before the mixed mode flow through step. In certain embodiments, the downstream processing includes a step of adding a surfactant (e.g., a detergent) to the rC7 composition, preferably to the rC7-containing effluent from the mixed mode flow through step. In certain embodiments, the downstream processing includes an irradiation step before the mixed mode flow through step and a step of adding a surfactant (e.g., a detergent) to the effluent from the mixed mode flow through step.

When the viral reduction step comprises the physical removal of the virus from the composition, typically filtering is involved. Specifically, nanofiltration comprises passing the composition through a matrix having a pore size of, e.g., 75 nm or less, 50 nm or less, 35 nm or less, or 15 nm or less, to separate the virus from the rC7. In certain embodiments, the downstream processing includes a viral removal step after the hydrophobic interaction chromatography step and before the UF/DF step, preferably using a porous filter having a mean pore size of 35 nm. Various nanofilters are available commercially and are known in the art.

In certain embodiments, the downstream processing includes a first viral reduction step comprising irradiating the composition before the mixed mode flow through step, a second viral reduction step comprising adding a surfactant (e.g., a detergent) to the effluent from the mixed mode flow through step, and a third viral reduction step comprising subjecting the flow through (effluent) from the hydrophobic interaction chromatography resin to a filter, preferably a porous filter having a mean pore size of 35 nm.

g. Endonuclease

In certain embodiments, the downstream processing includes a step of treating a rC7-containing composition with an endonuclease. The endonuclease is preferably one that degrades both DNA and RNA. In one embodiment, the endonuclease is a genetically engineered endonuclease from *Serratia marcescens* (Eaves, G. N. et al. *J. Bact.* 1963, 85, 273-278; Nestle, M. et al. *J. Biol. Chem.* 1969, 244, 5219-5225) that is sold under the name Benzonase® (EMD Millipore). The enzyme is produced and purified from *E. coli* strain W3110, a mutant of strain K12, containing the pNUC1 production plasmid (U.S. Pat. No. 5,173,418, which is hereby incorporated by reference in its entirety). Structurally, the protein is a dimer of identical 245 amino acid, about 30 kDa subunits with two important disulfide bonds. Benzonase® degrades all forms of DNA and RNA (single stranded, double stranded, linear and circular) and is effective over a wide range of operating conditions, digesting nucleic acids to 5'-monophosphate terminated oligonucleotides 2-5 bases in length. Benzonase® is produced under current good manufacturing practices (cGMP) and, thus, can be used in commercial scale processes for the purification of pharmaceutical proteins.

Other endonucleases that are produced under cGMP conditions can likewise be used in the purification methods disclosed in this application, including, but not limited to Denerase (Sartorius Stedim Biotech, Gottingen, Germany), Cyanase (RiboSolution, Cedar Creek, Tex., USA.) and PierceUniversal Nuclease (Thermo Scientific, Waltham, Mass., USA).

In certain embodiments, the endonuclease treatment step occurs before the hydrophobic interaction chromatography step. In certain embodiments, the endonuclease treatment step occurs after the cation exchange chromatography step. In certain embodiments, the endonuclease treatment step occurs after the cation exchange chromatography step and before the hydrophobic interaction chromatography step.

6. Pharmaceutical Compositions

The rC7 purified according to the present disclosure can be formulated according to known methods to prepare pharmaceutically useful compositions. The compositions of the disclosure can be formulated for administration to a mammalian subject, preferably a human, using techniques known in the art. In particular delivery systems may be formulated for intramuscular, intradermal, mucosal, subcutaneous, intravenous, injectable depot type devices or topical administration. When the delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. The compositions may also contain other pharmaceutically acceptable excipients, including, for example, alumina, aluminum stearate, lecithin, serum proteins, such as human serum albumin, phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, zinc salts, colloidal silica, magnesium trisilicate, polyvinyl pyrrolidone, cellulose-based substances, polyethylene glycol, sodium carboxymethylcellulose, polyacrylates, polyethylene-polyoxypropylene-block polymers, and polyethylene glycol.

In certain embodiments, the pharmaceutical composition obtained by the purification methods described herein comprises rC7, sodium phosphate, sodium citrate, sodium chloride, arginine, a sugar (e.g., sucrose), and a surfactant (e.g., a polysorbate).

In certain embodiments, the pharmaceutical composition obtained by the purification methods described herein contains no more than 2000 ng of host cell protein per mg rC7, preferably no more than 1000 ng/mg, and more preferably no more than 600 ng/mg.

In certain embodiments, the pharmaceutical composition obtained by the purification methods described herein contains no more than 42 pg host cell DNA per mg rC7, preferably no more than 25 pg/mg, and more preferably no more than 15 pg/mg.

In certain embodiments, the pharmaceutical composition obtained by the purification methods described herein contains no more than 1.0 EU/mg endotoxin per mg rC7, preferably no more than 0.70 EU/mg, and more preferably no more than 0.50 EU/mg.

The pharmaceutical compositions also have high purity with respect to viruses. The processes described herein yield significant virus log 10 reduction values (LRV). For example, the process delivers LRV>18 and LRV>4 for the xenotrophic murine leukemia virus and the porcine parvovirus, respectively.

The present disclosure will be more fully understood by reference to the following Examples.

EXAMPLES

Example 1: Upstream Processing

A first run and a second run were successfully completed through 20 clarified harvests with 10 captures by ultrafiltration/diafiltration (UF/DF) in order to produce unpurified bulk (UPB). The UF/DF was performed via tangential flow filtration (TFF). A total of 2241 L of UPB containing 102.9 grams of rC7 from the first run and 1052 L of UPB containing 92.1 g of rC7 from the second run were produced for downstream processing, representing an average yield of 70% for clarification and 60% for the capture process.

A 2000 L production bioreactor was inoculated with a seed culture. After inoculation, the rC7 production bioreactor culture was grown (1500 L working volume) in batch phase with no perfusion. At the end of the batch phase, perfusion growth phase was initiated, followed by a production phase (20 consecutive days), and daily harvest collection. Clarification operations were performed daily for each individual harvest pool for each run.

The harvests were clarified to remove cells, cellular debris and reduce bioburden, plus other particulates, prior to UF/DF capture. Unprocessed bulk from the bioreactor was collected in a 3000 L bag contained within a jacketed tote. Upon completion of the harvest collection, the unclarified harvest was maintained at 2-8° C. Each harvest was clarified as a batch on a daily basis using a clarification train, which included a Millipore DOHC Pod depth filters, Millipore DE50 Pod depth filters, Sartorius Sartopure GF plus 0.65 µm depth filters, Sartorius Sartoguard PES nominal 1.2/0.2 µm membrane filters, and Sartorius Sartopore PES Platinum 0.45/0.2 µm sterilization grade filters.

The clarified harvest was then concentrated by ultrafiltration (UF), followed by diafiltration (DF) and further concentrated to generate an unpurified bulk liquid for downstream purification. The UF/DF steps were carried out using an UF membrane comprised of regenerated cellulose (Sartorius-Stedim). The UF membrane was contained in TFF Hydrosart cassettes with an ECO screen channel design (100 kDa MWCO Hydrosart ECO). The UF/DF steps remove low molecular components, reduce levels of host cell proteins present in the clarified harvest, reduce the volume of the clarified harvest and achieve the desired UPB pH and conductivity. Each UF/DF capture operation combined two contiguous clarified harvest pools. Thus, with 20 clarified harvests, a total of 10 capture runs were performed. The material that is retained by the membrane is called the retentate. In this system, it was unexpectedly discovered that the rC7 concentrates in a layer adjacent to the membrane rather than collecting in the retentate. Accordingly, the initial retentate was drained from the system. The rC7 in the layer was resolubilized by adding 0.02M Tris, 0.15M NaCl, 0.1M L-arginine, 0.01% Triton X-100, pH 8.0 and recirculating throughout the system to obtain a second retentate comprising rC7.

The rC7 in the second retentate was diafiltered using the same solution (0.02M Tris, 0.15M NaCl, 0.1M L-arginine, 0.01% Triton X-100, pH 8.0), and rC7 was retained by the 100 kDa membrane. The diafiltered product was then concentrated to a target volume of 75 L of unpurified bulk (UPB). The concentrated and diafiltered harvest was recovered from the system by transferring to a mix station. Next, a system rinse was performed (target addition of 35 L), again with the same buffer solution to recover residual product from the system and then used to dilute the more concentrated product to a final target of approximately 105 L. The diluted product was mixed and filtered through a 0.45/0.2 µm filter and filled into 20 L bioprocess bags to a volume between 7 and 11 L. The filled bags were stored in a freezer at −20±5° C. for less than 5 days followed by long term storage at −50±5° C. until downstream processing.

Between the two runs, a total of 3292.3 L of UPB containing 195 grams of rC7 was captured, representing an average recovery yield of about 70% for the clarification step and about 60% for capture (UF/DF) step. By comparison, the rC7 recovery for the capture (UF/DF) step in our previous, internal upstream processing, where rC7 was collected in the initial retentate, was only about 24%. Thus, the current capture step provides a major improvement in rC7 recovery during the commercial scale production of rC7, resulting in significant increases in yield and cost savings. The total rC7 production for the clarification and UF/DF capture (upstream process) is summarized in Table 1 and FIG. 4.

TABLE 1 rC7 Titer results and total UPB production

| | Run 1 | | | Run 2 | | |
|---|---|---|---|---|---|---|
| Harvest # | UPB Volume (L) | UPB Titer (mg/L) | Total rC7 (g) | UPB Volume (L) | UPB Titer (mg/mL) | Total rC7 (g) |
| H1-2 | 307 | 18.7 | 5.7 | 103.2 | 54.8 | 5.7 |
| H3-4 | 307 | 28.8 | 8.8 | 105.7 | 92.4 | 9.8 |
| H5-6 | 308 | 33.7 | 10.4 | 105.5 | 98.2 | 10.4 |
| H7-8 | 302.2 | 29.7 | 9.0 | 107 | 94.5 | 10.1 |
| H9-10 | 298.8 | 45.9 | 13.7 | 103.1 | 138.0 | 14.2 |
| H11-12 | 298.9 | 45.9 | 13.7 | 102.8 | 102.2 | 10.5 |
| H13-14 | 104.7 | 99.7 | 10.4 | 104.7 | 80.4 | 8.4 |
| H15-16 | 105 | 111.9 | 11.7 | 105.5 | 71.0 | 7.5 |
| H17-18 | 105.2 | 98.9 | 10.4 | 106.5 | 66.6 | 7.1 |
| H19-20 | 103.9 | 85.8 | 8.9 | 107.6 | 78.8 | 8.5 |
| Total | 2240.7 | — | 102.9 | 1051.6 | — | 92.1 |

Figure 5:
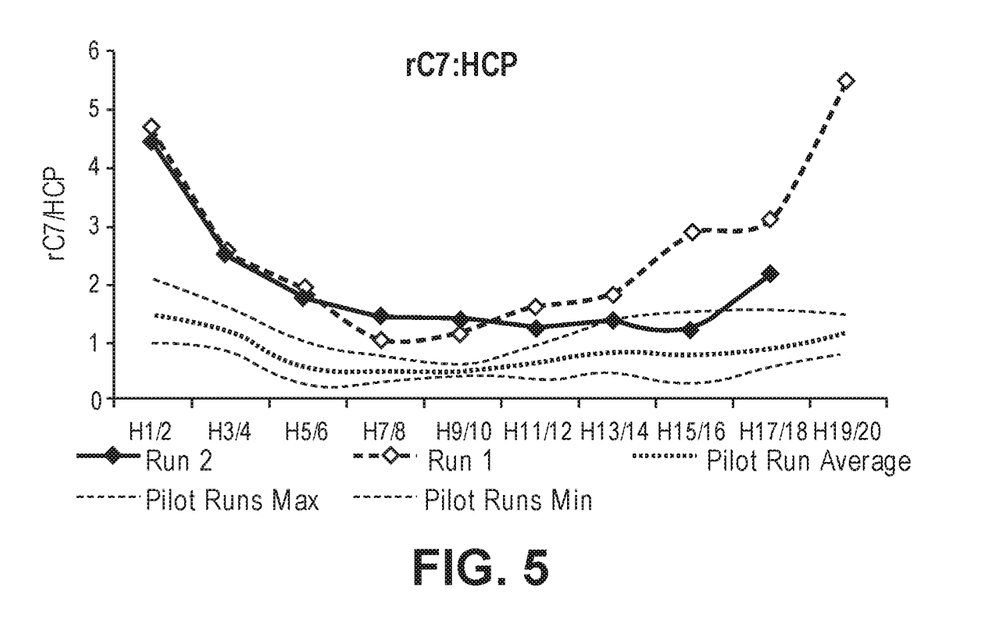
FIG. 5 shows the rC7/host cell protein (HCP) in the unpurified bulk (UPB) obtained from the harvests of a first and second production run (20 daily harvest total), following the clarification and UF/DF steps (upstream process). Average rC7/HCP ratios (and maximum and minimum values) from pilot runs are also provided.

Lastly, as a measure of UPB quality, the ratio of rC7 to host cell protein (HCP) was evaluated as a simple measure of purity. FIG. 5 summarizes the rC7:HCP ratio for the two runs, showing higher rC7:HCP values for both early and late harvests.

Example 2 Downstream Processing

Figure 6:
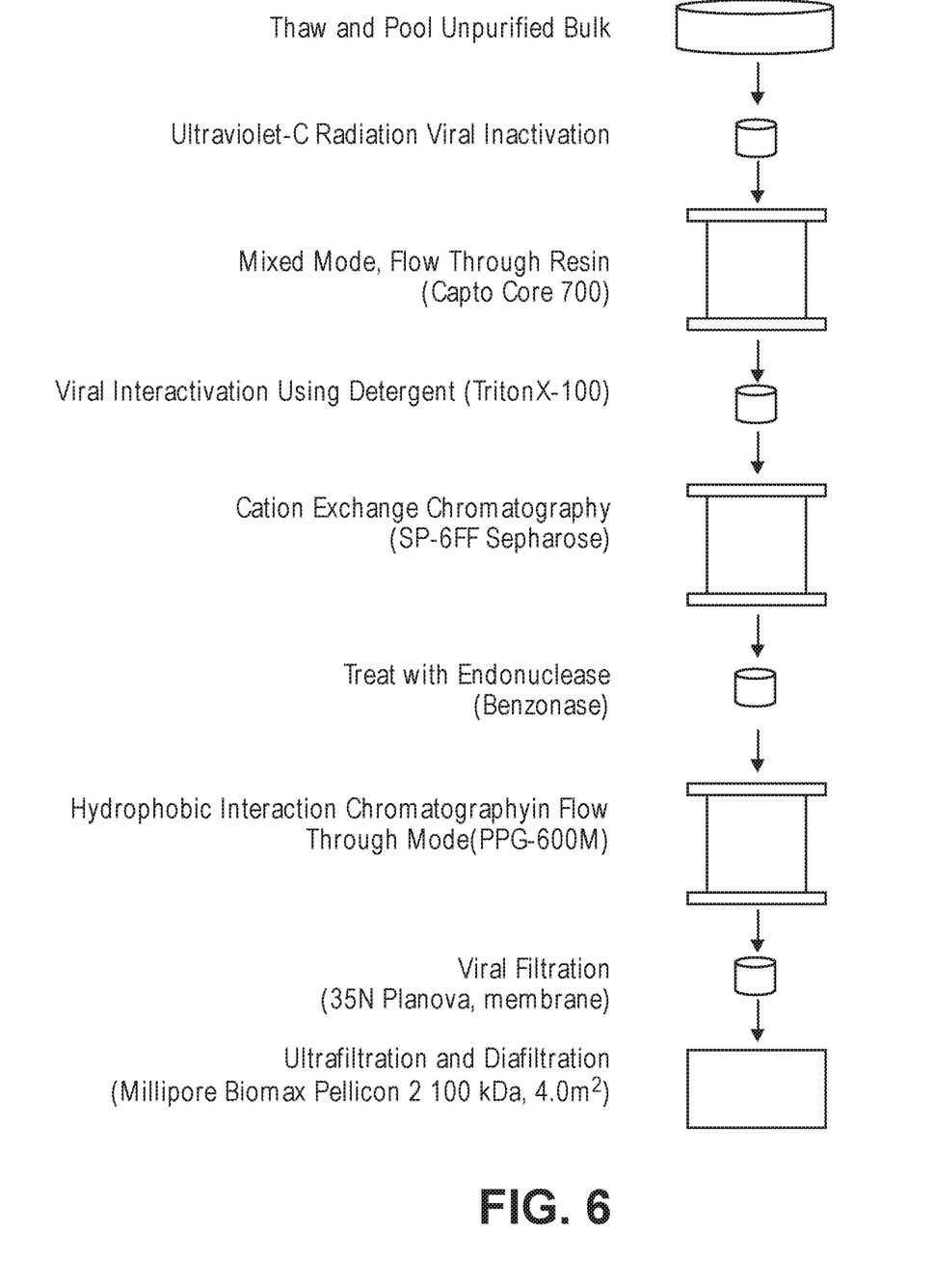
FIG. 6 is a schematic showing one embodiment of the rC7 purification method (downstream process).

A generalized schematic of a rC7 purification process is presented in FIG. 6. The unpurified bulk (UPB) from Example 1 was thawed and pooled to target a CAPTO Core 700 (GE Healthcare Life Sciences) specified load. The intended target CAPTO Core 700 (GE Healthcare Life Sciences) load is 1.0 g rC7 per L resin (assuming 100% titer yield for UPB filtration and ultraviolet-C operations). The loading specifics are detailed in Table 2 below.

TABLE 2

UPB Pooling and Capto Core Column Load

| Downstream Run # | UPB Pooled Volume (L) | Avg. UPB Titer (mg/L) | Total rC7 (g) | Capto Core CV (L) | Capto Core Load (g/L) |
|---|---|---|---|---|---|
| DS Run 1 | 114 | 229 | 26.1 | 26.0 | 1.00 |
| DS Run 2 | 141 | 194 | 27.4 | 27.0 | 1.01 |

The pooled UPB was filtered through a 0.45 and 0.2 µm filter to remove particulates and reduce bioburden in preparation for downstream processing. The filtered UPB was subjected to ultraviolet C irradiation using a UVIVATEC (Sartorius) system. The viral inactivated UPB was pooled and filtered through a 0.2 µm filter.

The first downstream column step for the purification process is a mixed mode resin, such as the CAPTO Core 700 (GE Healthcare Life Sciences) column, in flow through mode. Impurities are bound to the resin while rC7 flows through. The solution used for column equilibration and washing comprised 0.02M Tris, 0.15M NaCl, 0.1M L-arginine and 0.01% Triton-X.

The flow through from the CAPTO Core 700 (GE healthcare Sciences) was treated with 1% Triton X-100 at ambient temperature for 3 to 24 hours to target enveloped virus particles and produce a viral inactivated (VI) pool.

The second chromatography step is a cation exchange chromatography step. Sulfopropyl (SP) Sepharose Fast Flow (GE healthcare Sciences) resin was used in this step. The VI pool was diluted by addition of 6M Urea to a final target concentration of 2M. The pool was then further adjusted to pH 4.8 using 1M acetic acid and filtered with 0.45 and 0.2 μm filters prior to loading on the SP resin. The SP column was equilibrated and washed with a solution comprising 0.066M L-arginine, 0.1M NaCl, 2M urea, and 0.02M acetate. The SP column was operated in the bind and elute mode with the rC7 binding to the cation exchange chromatography resin. The loading, wash, and elution were all performed at constant flowrate. rC7 was eluted from the column with a solution comprising 0.066M L-arginine, 0.22M NaCl, 2M urea, and 0.02M acetate. No fractionation of the elution pool was performed.

Following the SP chromatography step, the SP elution pool was adjusted to pH 8.0 using 1M Tris base. The pool was then adjusted further with 1M MgCl$_2$ to a final concentration of 2 mM. The intermediate was then 0.45/0.2 m filtered and heated to 30° C. Benzonase™ (EMD Millipore) endonuclease was added to start the DNA digestion reaction, and the reaction mixture was held for 16-20 hrs.

The third chromatography step is a hydrophobic interaction column. A Toyopearl PPG 600M (Tosoh Biosciences) resin was used in flow through mode. The Benzonase™ treated pool was cooled to 18° C. and then adjusted to pH 6.0 using 1M MES, acid. 5M NaCl was then added to a final concentration of 1.5M and filtered through a 0.45/0.2 μm filter, prior to loading on the PPG column. Impurities bind to the resin while rC7 flows through the column at pH 6.0 in 0.02M MES, 1.5M NaCl. Flow through collection began at 0.4 CV after the start of the load and ended after 1.5 CV of wash.

The collected FT/W pool was adjusted with 0.75M L-Arginine, HCl to a final concentration of 0.1M and filtered through a 0.45/0.2 μm filter, prior to passage through a Planova-N35 nanofilter (Asahi Kaei Medical, Japan) to remove virus-like particles nominally larger than 35 nM from the process stream.

The final formulation and concentration step is a UF/DF step. The viral filtered pool was loaded onto the 4 m$^2$ TFF system, concentrated to 0.2 mg/mL and diafiltered with 6-8 diavolumes of 0.07M NaCl, 0.005M Citrate, 0.01M sodium phosphate, 0.1M L-arginine, and 0.05M sucrose using a Biomax Pellicon 2 100 kDa UF/DF membrane (EMD Millipore). Upon completion of diafiltration, the material was recovered via draining and a system rinse and subsequently pooled. The pooled product was then further concentrated to 1.4 mg/mL using a 2.5 m$^2$ TFF system.

Polysorbate 80 was added from a 20% stock solution to a final concentration of 0.05%. The resultant rC7 pool was filtered through a 0.5/0.2 μm filter, prior to dispensing into 1L bottles to a target fill volume of 300 mL and stored between −65 to −85° C.

5.4 and 4.7 grams of rC7 were obtained from the DS-1 and DS-2 runs, respectively, amounting to a rC7 recovery rate of 21% and 17% respectively, as compared to the amount of rC7 in the UPB, as summarized in Table 3 below. By comparison, the rC7 recovery in our prior, internal downstream purification process was only about 2%. Thus, the recovery rate of the current rC7 downstream purification process is about 10-fold more than our previous internal process, providing significant advances in yield and cost savings.

TABLE 3

Downstream rC7 Recovery

| Downstream Run # | Total rC7 in UPB by Titer ELISA (g) | Total rC7 DS Produced by A280 (g) | rC7 Recovery (%) |
|---|---|---|---|
| DS Run 1 | 26.1 | 5.4 | 21 |
| DS Run 2 | 27.4 | 4.7 | 17 |

The resulting rC7 recovered by this purification process also met all quality specifications, including fibronectin binding and the purity requirements as summarized in Table 4 below.

TABLE 4 rC7 purity

| Quality Attribute | Specification | DS Run 1 | DS Run 2 |
|---|---|---|---|
| Protein Conc. (mg/mL) | 1.20 ± 0.25 mg/mL | 1.17 | 1.2 |
| pH | 7.2 ± 0.3 | 7.38 | 7.36 |
| Osmolality | 420 ± 60 mOsm/kg | 405 | 409 |
| Color/Appearance | | Conforms | Conforms |
| Host Cell Protein ng/mg | ≤2000 ng/mg | 618 | 644 |
| Residual DNA pg/mg | ≤42 pg/mg | 9 | 10 |
| % HMW | ≤25.0% | 18.6 | 16.6 |
| % Main Peak | ≥40.0% | 69.9 | 69.4 |
| % LMW | | 11.5 | 14 |
| Endotoxin | ≤1.0 EU/mg | <0.34 | <0.17 |
| Bioburden | ≤1 CFU/10 mL | 0 | 0 |
| Benzonase (ng/mg) | | 71 | 73 |
| Fibronectin Binding | | >100 (285) | >100 (179) |
| C7 Identity Confirmation | | Conforms | Conforms |
| Process and Product-related impurities | | Conforms | Conforms |

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Unless otherwise indicated, all numbers used in the specification and claims are to be understood as being modified in all instances by the term "about," whether or not so stated. It should also be understood that the precise numerical values used in the specification and claims form additional embodiments of the disclosure, as do all ranges and subranges within any specified endpoints. In addition, it will be noted that where steps are disclosed, the steps need not be performed in that order unless explicitly stated.

Other embodiments will be apparent to those skilled in the art from consideration of the specification and practice of the disclosure.

REFERENCES

1. Burgeson R. E., Chapter 4C. Type VII Collagen in Extracellular Matrix A Practical Approach, Haralson M. A. and Hassell J. R. Eds., Oxford University Press, 1995.
2. Chen M. et al, J. Biol. Chem. 277 (2002) 2118-2124.

We claim:

1. A method for capturing recombinant collagen 7 product from a cell culture, the method comprising:
   a) subjecting a supernatant harvested from the cell culture to a depth filter, wherein the supernatant contains recombinant human collagen 7;
   b) collecting a solution that flows through the depth filter;
   c) subjecting the solution from step b) to an ultrafiltration step, wherein the recombinant human collagen 7 concentrates in a layer adjacent to an ultrafiltration membrane;
   d) discarding a first retentate, wherein the first retentate comprises impurities contained in the solution from step b);
   e) subjecting the layer adjacent to the ultrafiltration membrane to a solubilization agent and/or a surfactant to recover recombinant human collagen 7 and to obtain a second retentate comprising recombinant human collagen 7;
   f) subjecting the second retentate to a diafiltration step to obtain an unpurified bulk liquid comprising recombinant collagen 7; and
   g) optionally freezing the unpurified bulk liquid,
   wherein the solubilization agent comprises at least one of urea, thiourea, arginine, butanol, ethanol, lithium perchlorate, lithium acetate, magnesium acetate, phenol, propanol, sodium dodecyl sulfate, aspartic acid, glutamic acid, ascorbic acid, glutamine, asparagine, and guanidine.

2. The method of claim 1, further comprising before step a), the steps of:
   I) culturing host cells that produce recombinant human collagen 7; and
   II) harvesting supernatant from the cultured host cells.

3. The method of claim 2, wherein the unpurified bulk liquid contains 40-80% of the recombinant human collagen 7 in the supernatant collected from step II).

4. The method of claim 3, wherein the cell culture comprises culturing host cells in a bioreactor with a volume of at least 200 liters.

5. The method of claim 4, wherein the bioreactor is a perfusion bioreactor or a fed-batch bioreactor.

6. The method of claim 5, wherein the unpurified bulk liquid contains over 50 grams of recombinant human collagen 7.

7. The method of claim 1, wherein the solubilization agent comprises arginine.

8. A method for purifying recombinant human collagen 7, the method comprising:
   a) subjecting a sample containing recombinant human collagen 7 to a mixed mode, flow through resin, wherein the mixed mode, flow through resin comprises a ligand activated core and an inactive shell, wherein the inactive shell prevents recombinant human collagen 7 from entering the ligand activated core and wherein impurities that are small enough pass through the inactive shell and bind to the ligand activated core;
   b) collecting a first effluent that flows through the mixed mode, flow through resin and contains recombinant human collagen 7;
   c) subjecting the first effluent from step b) to a cation exchange chromatography resin under conditions permitting the recombinant human collagen 7 to bind to the cation exchange chromatography resin;
   d) eluting recombinant human collagen 7 from the cation exchange chromatography resin;
   e) subjecting the eluted recombinant human collagen 7 from step d) to a hydrophobic interaction chromatography resin in flow through mode and collecting a second effluent that flows through the hydrophobic interaction chromatography resin;
   f) adding a solubilization agent and/or surfactant to the second effluent from step e) prior to step g);
   g) subjecting the second effluent of step f) to an ultrafiltration step to concentrate the recombinant human collagen 7;
   h) dialfiltering the concentrated recombinant human collagen 7 from step g) with a buffer comprising at least one salt, a solubilization agent, and a sugar; and
   i) recovering purified recombinant human collagen 7,
   wherein the method comprises one or more viral reduction steps and an endonuclease treatment step.

9. The method of claim 8, wherein the ultrafiltration step comprises a tangential flow filter and wherein the tangential flow filter comprises a hydrophilic membrane.

10. The method of claim 8, wherein the one or more viral reduction steps comprise a step of irradiating the sample containing recombinant human collagen 7 prior to step a), a step of adding a surfactant to the first effluent from step b), and a step subjecting the second effluent from step e) to a porous filter.

11. The method of claim 10, wherein the endonuclease treatment step comprises treating the eluted recombinant human collagen 7 from step d) with an endonuclease.

12. The method of claim 8, wherein the solubilization agent comprises at least one of urea, thiourea, arginine, butanol, ethanol, lithium perchlorate, lithium acetate, magnesium acetate, phenol, propanol, sodium dodecyl sulfate, aspartic acid, glutamic acid, ascorbic acid, glutamine, asparagine, and guanidine.

13. The method of claim 12, wherein the at least one salt is one or more of sodium chloride, citrate, and sodium phosphate, the solubilization agent is arginine, and the sugar is sucrose.

14. The method of claim 13, wherein the purified recombinant human collagen 7 of step i) contains on average between 15-30% of the amount of the recombinant human collagen 7 in the sample from step a).

15. The method of claim 14, wherein the sample in step a) contains at least 25 grams of recombinant human collagen 7.

16. The method of claim 15, wherein at least 4.0 grams of purified recombinant human collagen 7 is recovered in step i).

17. The method of claim 16, wherein the purified recombinant human collagen 7 of step i) contains no more than 600 ng/mg.

18. The method of claim 17, wherein the purified recombinant human collagen 7 of step i) contains no more than 15 pg/mg.

19. The method of claim 18, wherein the purified recombinant human collagen 7 of step i) contains no more than 0.50 EU/mg.

20. The method of claim 19, further comprising before step a), the steps of:
I) subjecting a supernatant harvested from a cell culture to a depth filter, wherein the supernatant contains recombinant human collagen 7;
II) collecting a solution that flows through the depth filter;
III) subjecting the solution from step b) to an ultrafiltration step, wherein the recombinant human collagen 7 concentrates in a layer adjacent to the ultrafiltration membrane;
IV) discarding a first retentate, wherein the first retentate comprises impurities contained in the solution from step II);
V) subjecting the layer adjacent to the ultrafiltration membrane to a solubilization agent and/or a surfactant to recover recombinant human collagen 7 and to obtain a second retentate comprising recombinant human collagen 7;
VI) subjecting the second retentate to a diafiltration step to obtain an unpurified bulk liquid comprising recombinant human collagen 7; and
VII) optionally freezing the unpurified bulk liquid,
wherein the solubilization agent comprises at least one of urea, thiourea, arginine, butanol ethanol lithium perchlorate, lithium acetate, magnesium acetate, phenol propanol sodium dodecyl sulfate, aspartic acid, glutamic acid, ascorbic acid, glutamine, asparagine, and guanidine.

21. The method of claim 20, wherein the solubilization agent comprises arginine.

* * * * *